(12) United States Patent
Sakakibara et al.

(10) Patent No.: US 11,071,616 B2
(45) Date of Patent: Jul. 27, 2021

(54) FILTER DEVICE

(71) Applicant: Toray Industries, Inc., Tokyo (JP)

(72) Inventors: Hajime Sakakibara, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 101 days.

(21) Appl. No.: 16/620,902

(22) PCT Filed: Jul. 27, 2018

(86) PCT No.: PCT/JP2018/028213
§ 371 (c)(1),
(2) Date: Dec. 10, 2019

(87) PCT Pub. No.: WO2019/022224
PCT Pub. Date: Jan. 31, 2019

(65) Prior Publication Data
US 2020/0205960 A1    Jul. 2, 2020

(30) Foreign Application Priority Data

Jul. 27, 2017 (JP) .............................. JP2017-145440

(51) Int. Cl.
*A61F 2/01* (2006.01)
*A61B 17/3207* (2006.01)

(52) U.S. Cl.
CPC .......... *A61F 2/013* (2013.01); *A61B 17/3207* (2013.01); *A61F 2/0108* (2020.05); *A61F 2/011* (2020.05); *A61F 2002/015* (2013.01)

(58) Field of Classification Search
CPC .. A61F 2/013; A61F 2/01; A61F 2/014; A61F 2/011; A61F 2/0105;
(Continued)

(56) References Cited

U.S. PATENT DOCUMENTS 5,954,745 A * 9/1999 Gertler .................... A61F 2/01
606/200
6,740,061 B1    5/2004 Oslund et al.
(Continued)

FOREIGN PATENT DOCUMENTS

JP    2007-325893 A    12/2007
JP      4067353 B2     1/2008
(Continued)

OTHER PUBLICATIONS

The Extended European Search Report dated Mar. 24, 2021, counterpart of European Application No. 18837831.9.

*Primary Examiner* — Jocelin C Tanner
(74) *Attorney, Agent, or Firm* — DLA Piper LLP (US)

(57) ABSTRACT

A filter device includes: a core member; a push member; first, second and third tubes; a first restriction member disposed on the first tube and configured to restrict a pushing movement of the third tube to the distal direction; a filter; a ring fixed to the opening; first and second wires, wherein the filter is configured in such a manner that the diameter of the opening is reduced by deformation of the shape of the ring, the deformation being caused by the first wires and the second wires when the push member fixed to the core member is pushed with the push member in contact with the second tube, and in such a manner that the diameter of the opening is expanded by restoration of the ring to the original shape, the restoration being caused by separating the push member fixed to the core member from the second tube.

6 Claims, 6 Drawing Sheets

(58) Field of Classification Search
CPC .......... A61F 2002/015; A61F 2002/016; A61F 2/0108; A61F 2/0103; A61F 2002/018; A61B 17/3207
See application file for complete search history.

(56) References Cited

U.S. PATENT DOCUMENTS

| | | | |
|---|---|---|---|
| 2004/0127933 A1* | 7/2004 | Demond | A61F 2/011 606/200 |
| 2007/0118173 A1* | 5/2007 | Magnuson | A61F 2/0108 606/200 |
| 2007/0185525 A1* | 8/2007 | White | A61F 2/011 606/200 |
| 2007/0239198 A1* | 10/2007 | Brounstein | A61F 2/0105 606/200 |
| 2010/0010534 A1* | 1/2010 | Mujkanovic | A61F 2/01 606/200 |
| 2014/0236220 A1 | 8/2014 | Inoue | |
| 2016/0008121 A1 | 1/2016 | Inoue | |
| 2018/0200040 A1* | 7/2018 | WasDyke | A61F 2/013 |

FOREIGN PATENT DOCUMENTS

| | | |
|---|---|---|
| JP | 5100933 B2 | 10/2012 |
| JP | 2016-016197 A | 2/2016 |
| JP | 5998147 B2 | 9/2016 |
| WO | 2016/067646 A1 | 5/2016 |

\* cited by examiner

FILTER DEVICE

TECHNICAL FIELD

This disclosure relates to a filter device for protection of peripheral vessels.

BACKGROUND

Lower-extremity arteriosclerosis obliterans (ASO) is a disease in which arteriosclerosis causes blood vessels to be constricted or occluded, resulting in lower-extremities developing an ischemic symptom. In a worst case, legs become gangrened and need to be amputated. At present, an endovascular treatment based on the use of a catheter is proposed as a therapeutic strategy. Among others, atherectomy is used to resect hard lesion sites highly calcified by advanced arteriosclerosis.

However, a risk has been pointed out that emboli such as resected pieces generated in an atherectomy surgery will be carried away downstream and cause infarction in peripheral vessels. Because of this, it is recommended that some atherectomy devices are each used together with a filter device for protection of peripheral vessels so that a risk of infarction in peripheral vessels can be avoided.

As such a filter device for protection of peripheral vessels as above-mentioned, there is a report on an improved distal protection device in which the improved distal protection device includes: a guidewire; a tube for receiving the guide wire; a filter basket connected to the tube and having a closed distal end and an open proximal end; and a spacing member connected to the tube and positioned proximally of the proximal end of the filter basket, the spacing member configured to maintain the proximal end of the filter basket in an opened configuration when the distal protection device is deployed within a vessel; wherein the end of the filter basket is freely movable along the guidewire (JP 5100933 B2). That improved distal protection device makes it possible that the device itself is used as a guidewire and, thus, an atherectomy device can be delivered to a target affected site along the distal protection device. In addition, the filter basket of the improved distal protection device is not only freely rotatable about the axis but also movable along the axis and, thus, is never ganged by any predetermined range of movement performed during a surgery such as a rotational movement or a forward movement, when the improved distal protection device is used together with an atherectomy device.

On the other hand, a plurality of similar filter devices for protection of blood vessels are also known in fields of application in which the devices are not used together with an atherectomy device. For example, there is a report on a filter device that can be indwelled in and pulled out of a blood vessel, which has a filter member whose opening can well contact the inner wall of an artery, and enables pieces of tissue to be securely captured. Disclosed as such a filter device is an intravascular blood filter including: a filter member; a forward traction wire connecting a filter opening/closing member provided on the opening of the filter member to a core member, which is a guidewire; and a backward traction wire connecting the filter opening/closing member to a catheter member; wherein the opening of the filter member can be opened and closed by deformation and restoration of the filter opening/closing member caused by the axial movement of the core member relative to the catheter member (JP 4067353 B2).

Also disclosed is a device that captures debris in blood vessels, the device including: a core wire arranged in a blood vessel; a filter member that includes a bag-like filter arranged in the blood vessel such that an opening faces an upstream side of blood flow, and a ring-like elastic wire rod attached around an opening edge part of the filter; linear bodies connecting the filter member to the core wire; and a slide tube inside which the core wire passes; wherein the device is configured such that, in moving the slide tube toward a fore end side of the core wire, the ring-like elastic wire rod is bent to hold the outer circumferential surface of the fore end part of the slide tube from radially outside, whereby the opening can be closed (JP 5998147 B2).

However, many atherectomy devices include a lumen into which a guidewire can be inserted and, because of this, it is desirable that a filter device for protection of peripheral vessels is used as a guidewire so that the atherectomy device can be delivered to a target affected site. In some instances in which an atherectomy surgery is performed, a plurality of lesion sites in a blood vessel are treated in the same maneuver and, thus, it is desirable that the indwelling position for a filter section can be changed easily.

If it is assumed that the improved distal protection device in JP '933 is used together with an atherectomy device, the filter basket has no mechanism to reduce the diameter of the opening and, thus, the atherectomy device must be pulled out of the body, followed by inserting a sheath to reduce the diameter of the filter basket to change the indwelling position of the filter basket whose diameter has been expanded against the blood vessel. Such a maneuver is complicated.

In addition, an intravascular blood filter described in JP '353 has traction wires fixed to the core member and the catheter member. If it is assumed that the intravascular blood filter is used together with an atherectomy device, it is possible that the filter is ganged by a rotational movement caused during an atherectomy surgery and, thus, that the traction wires are entwined with the core member or the catheter member. In that instance, it is possible that the opening of the filter section results in being insufficiently controlled, letting emboli such as resected pieces generated in a surgery pass downstream. Furthermore, if it is assumed that the core member is used as a guidewire function to guide the filter member to a target site, the core member used as the guidewire is rotated, making it likely that the traction wires are entwined with the core member or the catheter member. In that instance, it is possible that the opening of the filter section results in being insufficiently controlled, letting emboli generated in a surgery pass downstream.

In addition, a device for capturing debris in blood vessel described in JP '147 can itself be used also as a guidewire and, thus, can be used together with an atherectomy device, but linear bodies connecting the filter member to the core wire are fixed to the core wire. Therefore, when the device for capturing debris in blood vessel is used together with an atherectomy device, it is possible that the former device is ganged by a rotational movement caused during an atherectomy surgery and that the linear bodies are entwined with the core wire. It is thus possible that the opening of the filter section results in being insufficiently controlled, letting emboli such as resected pieces generated in a surgery pass downstream. Furthermore, when the device for capturing debris in blood vessels is indwelled in a curved portion of a blood vessel, forward movement of an atherectomy device causes the core wire to be moved toward the greater curvature side of the curved portion of the blood vessel, accompanied by ganged movement of the linear bodies connected to the core wire and the ring-like member connected to the linear bodies, whereby the ring-like elastic wire rod may be separated from the blood vessel wall. It is thus possible that emboli such as resected pieces generated in a surgery is let pass downstream.

It could therefore be helpful to provide a filter device that makes it possible to change the indwelling position of a filter section easily when the filter device is used together with an atherectomy device and that makes it possible to efficiently capture emboli such as resected pieces generated during an atherectomy surgery.

SUMMARY

We thus provide:

(1) A filter device includes: a core member; a push member fixed to the core member; a first tube disposed proximally of the push member in the longitudinal direction and movable along the core member; a second tube disposed distally of the push member in the longitudinal direction and movable along the core member; a third tube movable along the first tube; a first restriction member disposed on the first tube and configured to restrict a pushing movement of the third tube to the distal direction of the first restriction member; a filter having a closed end distally of the push member in the longitudinal direction and disposed to have an opening at the proximal end of the filter; a ring fixed to the opening and having elasticity or shape-memory ability; two first wires, one end of each first wire being fixed to the third tube, and the other end being fixed to part of the ring; and two second wires, one end of each second wire being fixed to part of the ring, and the other end being fixed to the second tube; wherein the filter is configured such that the diameter of the opening is reduced by deformation of the shape of the ring, the deformation being caused by the first wires and the second wires when the push member fixed to the core member is pushed with the push member in contact with the second tube, and such that the diameter of the opening is expanded by restoration of the ring to the original shape, the restoration being caused by separating the push member fixed to the core member from the second tube.

(2) The filter device according to (1), wherein the positions at which the first wires are fixed to the ring and the positions at which the second wires are fixed to the ring are arranged alternately in relation to the central axis of the core member.

(3) The filter device according to (1) or (2), wherein a second restriction member is fixed to the first tube and configured to restrict the movement of the third tube to a proximal portion of the first tube in the longitudinal direction.

(4) The filter device according to any one of (1) to (3), wherein a spring-like member is fixed to a proximal portion of the core member in the longitudinal direction.

(5) The filter device according to any one of (1) to (4), wherein a flexible member is fixed to a distal portion of the core member in the longitudinal direction.

(6) The filter device according to any one of (1) to 4, including: a double lumen tube having a first lumen into which a guidewire can be inserted and a second lumen into which the core member can be inserted, wherein the double lumen tube is fixed to a distal portion of the second tube in the longitudinal direction.

We make it possible for the body of the filter device to be used as a guidewire and an atherectomy device is delivered along the body of the filter device to a target affected site. In addition, our filter device makes it possible that emboli such as resected pieces carried away during an atherectomy surgery are captured efficiently by the filter disposed downstream.

REFERENCE SIGNS LIST

Figure 1:
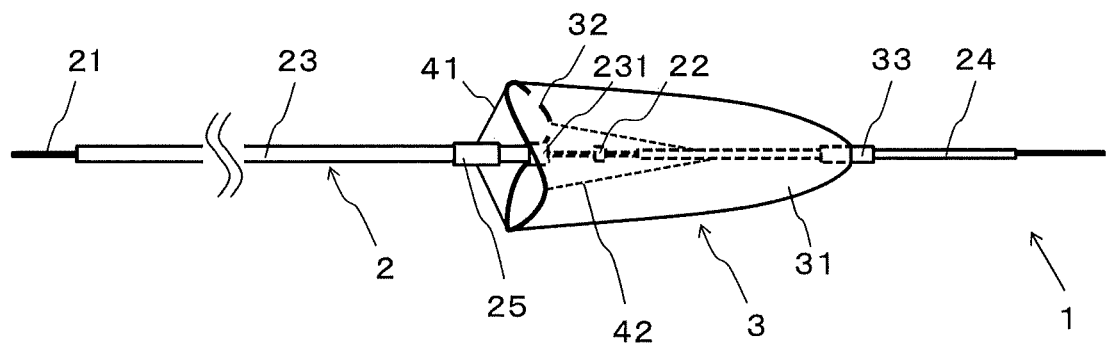
FIG. 1 is an explanatory view depicting a first example of a filter device.

1: Filter Device
2: Body Section
3: Filter Section
6: Intravascular Blood Filter
7: Mimic Blood Vessel Tube
8: Atherectomy device
9: Peripheral Protection Device
10, 11, 12, 13, 14: Filter Device
21: Core Member
22: Push Member
23: First Tube
24: Second Tube
25: Third Tube
26: Flexible Member
27: Double Lumen Tube
28: Spring Member
31: Filter
32: Ring
33: Movable Member
41: First Wire
42: Second Wire
61: Core Member
62: Catheter Member
63: Filter Member
64: Filter Ring
65: Forward Traction Wire
66: Backward Traction Wire
71: Mimic Blood Vessel Tube
91: Mimic Emboli Particle
231: First Restriction Member 232: Second Restriction Member
411: First Wire Group
421: Second Wire Group
271: First Lumen
272: Second Lumen

DETAILED DESCRIPTION

Below, specific examples will be described with reference to the drawings, but this disclosure is not limited to the examples. The proportions shown in the drawings do not necessarily accord with those mentioned in the description.

First Example

FIG. 1 is a schematic view of a filter device 1 according to a first example. The filter device 1 is used, for example, as a filter device for protection of peripheral vessels to prevent emboli such as resected pieces from being carried away into peripheral vessels and causing infarction in which the resected pieces are generated in performing an atherectomy surgery for treatment of lower-extremity arteriosclerosis obliterans. The filter device 1 according to the first example includes: a body section 2 for moving a filter section 3 to a target site in a blood vessel; the filter section 3 for capturing thrombi; first wires 41 and second wires 42 for adjusting the opening diameter of the opening of the filter section 3.

The body section 2 includes: a core member 21; a push member 22 fixed to the core member 21; a first tube 23 disposed proximally of the push member 22 in the longitudinal direction and movable along the core member 21; a second tube 24 disposed distally of the push member 22 in the longitudinal direction and movable along the core member 21; a third tube 25 movable along the first tube 23; a first restriction member 231 disposed on the first tube 23 and configured to restrict a pushing movement of the third tube 25 to the distal direction.

The material of the core member 21 is preferably such a metal as used as a general guidewire such as stainless steel, high-strength steel, tungsten, cobalt alloy, or nickel alloy.

The core member 21 preferably has a length of approximately 700 to 3000 mm and an outside diameter of approximately 0.1 to 0.3 mm, for example, when the filter device is used together with an atherectomy device.

Figure 2:
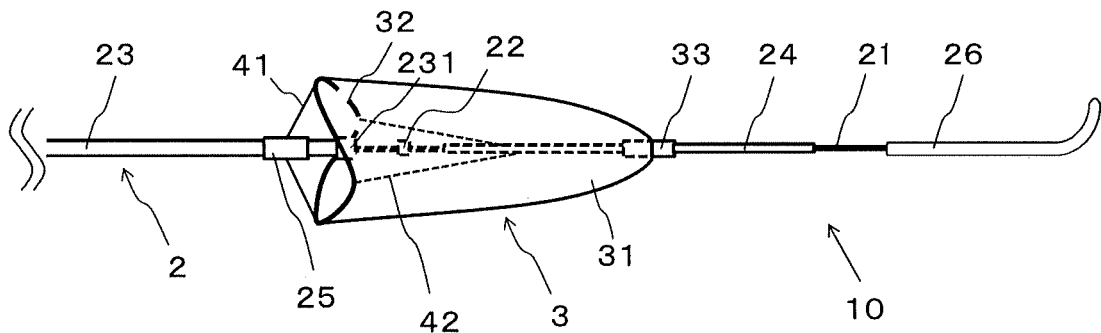
FIG. 2 is an explanatory view depicting a second example of a filter device.

A flexible member 26 may be provided on a distal portion of the core member 21 in the longitudinal direction, as depicted in FIG. 2, in a filter device 10 according to a second example different from the first example. This makes it possible to decrease injury to living tissue such as a blood vessel wall in inserting the filter device 10 into the blood vessel.

The flexible member 26 is possibly a coil joined around the periphery of the core member 21, wherein the coil is made of metal such as stainless steel, superelastic alloy, cobalt alloy, nickel alloy, gold, platinum, or tungsten. Alternatively, it is possible that a thermoplastic resin is joined to a distal portion of the core member 21, examples of such a thermoplastic resin including polyurethane, polyamide, silicone, polyolefins such as polypropylene and polyethylene, polyetherketone resins (PEEK), fluorine resins, ethylene-tetrafluoroethylene copolymers (ETFE), polytetrafluoroethylene (PTFE), and polyimide, which are flexible materials.

The material that can be used for the push member 22 may be any one of the materials that enable the push member 22 to push the second tube 24, and may be a metal such as stainless steel, high-strength steel, tungsten, cobalt alloy, or nickel alloy, or a thermoplastic resin such as polyurethane, polyamide, silicone, polyolefin such as polypropylene or polyethylene, polyetherketone resin (PEEK), fluorine resin, ethylene-tetrafluoroethylene copolymer (ETFE), polytetrafluoroethylene (PTFE), or polyimide.

The push member 22 has an outside diameter that only needs to be larger than the inside diameter of the second tube 24, and that is preferably, for example, approximately 0.6 mm at the maximum when the filter device is used together with an atherectomy device.

The materials that can be used for the first tube 23, the second tube 24, and the third tube 25 may each be any one of the materials having flexibility, and may be, for example, a thermoplastic resin such as polyurethane, polyamide, silicone, polyolefin such as polypropylene or polyethylene, polyetherketone resin (PEEK), fluorine resin, ethylene-tetrafluoroethylene copolymer (ETFE), polytetrafluoroethylene (PTFE), or polyimide.

When the material of the first tube 23 is a resin such as polyamide or polyimide, it is also possible that a highly slippery resin such as polytetrafluoroethylene is incorporated as an inner layer to enhance the slidability of the core member 21. It is also possible that a braided layer made using a metal wire such as of stainless steel or a resin such as polyamide is incorporated inside to secure rigidity.

The first tube 23 preferably has a length of approximately 600 to 1500 mm and an outside diameter of approximately 0.36 mm, for example, when the filter device is used together with an atherectomy device. This constitution enables the filter device to be used as a guidewire to convey an atherectomy device. The first tube 23 has an inside diameter that only needs to enable the core member 21 to smoothly slide through the first tube.

Furthermore, the surface of the first tube 23 preferably undergoes antithrombogenic treatment because thrombi are possibly adhered to or generated on the surface of the tube.

The first restriction member 231 has an outside diameter that only needs to be larger than the inside diameter of the third tube 25, and that is preferably approximately 1 mm at the maximum, for example, when the filter device is used together with an atherectomy device. This constitution makes it possible that, even if the third tube 25 is moved forward relative to the first tube 23, the third tube 25 is stopped by the first restriction member 231, and thus, that the movement of the third tube 25 in the longitudinally distal direction from the first tube 23 is restricted.

The second tube 24 preferably has a length of approximately 10 to 30 mm, for example, when the filter device is used together with an atherectomy device. In addition, the second tube 24 preferably has an outside diameter of approximately 0.2 to 0.5 mm and an inside diameter that only needs to enable the core member 21 to smoothly slide through the second tube.

Figure 3:
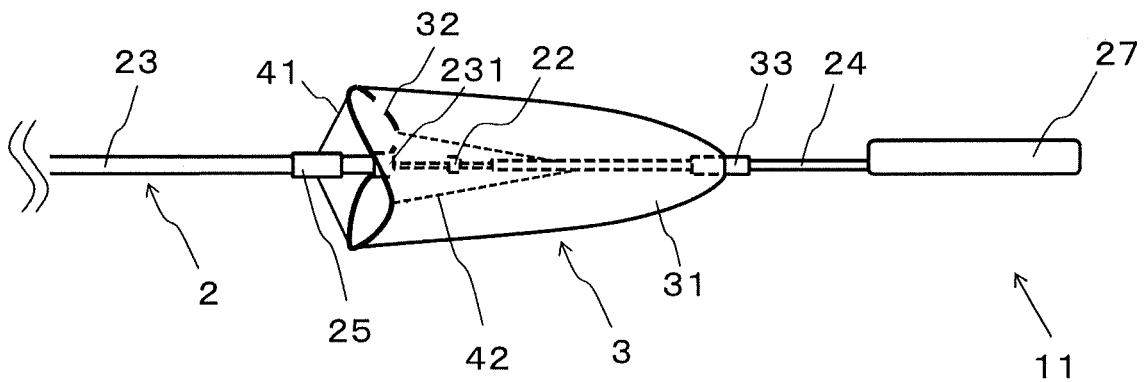
FIG. 3 is an explanatory view depicting a third example of a filter device.

In a filter device 11 according to a third example different from the first example, the second tube 24 may include a double lumen tube 27 on a distal portion of the core member 21 in the longitudinal direction, instead of providing the flexible member 26 on a distal portion of the core member 21 in the longitudinal direction, as depicted in FIG. 3. This double lumen tube 27 includes: a first lumen 271 into which a guidewire generally used for catheterization of the circulatory system can be inserted; and a second lumen 272 into which the second tube 24 can be inserted, as described in the internal structure of the distal portion in FIG. 4. When the double lumen tube 27 that includes the lumen 271 in which the core member 21 is movable and the lumen into which the guidewire can be inserted is on a distal portion of the second tube 24 in the longitudinal direction, the second tube 24 is inserted and fixed in the second lumen 272 and, in addition, the core member 21 is axially movable in the second lumen 272. With this constitution, the body section 2 can be moved along the previously indwelled guidewire so that the filter device 11 can be delivered to a target affected site.

Figure 4:
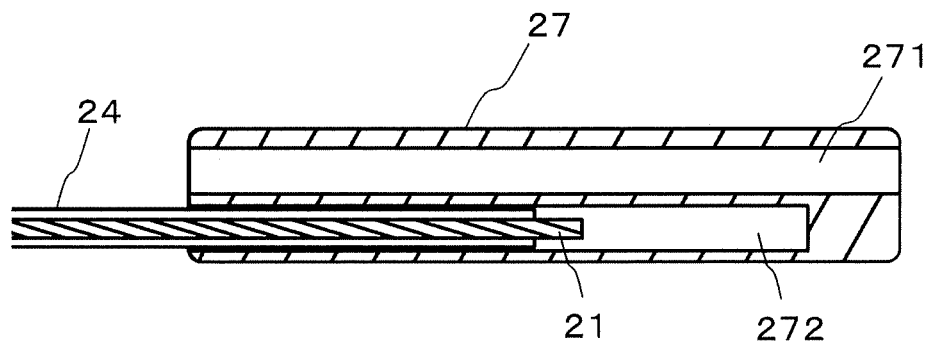
FIG. 4 is an explanatory view depicting the internal structure of a distal portion of a filter device according to the third example.

The second lumen 272 may be a through-hole, but is preferably a non-through-hole having a terminus in the double lumen tube, as described in FIG. 4. With this constitution, the core member 21, when moved forward, is not projected from the distal end of the double lumen tube 27, making it possible to decrease injury to living tissue such as a blood vessel wall.

The material that can be used for the double lumen tube 27 may be any one of the materials having flexibility and may be, for example, a thermoplastic resin such as polyurethane, polyamide, silicone, polyolefin such as polypropylene or polyethylene, polyetherketone resin (PEEK), fluorine resin, ethylene-tetrafluoroethylene copolymer (ETFE), polytetrafluoroethylene (PTFE), or polyimide.

The third tube 25 preferably has a length of approximately 1 to 10 mm and an outside diameter of approximately 0.5 to 1 mm, for example, when the filter device is used together with an atherectomy device. The third tube 25 has an inside diameter that only needs to enable the third tube 25 to smoothly slide along the first tube 23.

The filter section 3 includes a bag-like filter 31 and a ring 32 fixed to the opening of the filter 31 and contributing to the opening and closing of the opening. As described in FIG. 1, the filter 31 according to the first example is shaped to alternately have a plurality of mountains protruding in the longitudinally distal direction and a plurality of valleys sinking in the longitudinally proximal direction. The bottom of the bag is formed to be a closed end as the distal end in the longitudinal direction, and the opening of the bag is formed to be an opening as the proximal end in the longitudinal direction.

The filter 31 is disposed on a distal portion of the filter device 1 in the longitudinal direction. In addition, the closed end of the filter section 3 may be fixed to the second tube 24, but as described in FIG. 1, the closed end is preferably fixed to the core member 21 or to a member 33 slidable along the second tube 24. This constitution makes it possible that the movable member 33 moves along the core member 21 or the second tube 24, changing the length of the filter 31 in the longitudinal direction.

The filter 31 according to the first example is made in the form of a bag using a polymer sheet having a plurality of pores. However, the filter 31 may be made in the form of a bag using a polymer fiber mesh or a metal fiber mesh to increase the opening ratio of the filter and thus secure the amount of passage of blood.

The material to be used for the filter 31 may be a polymer such as polyester, polyurethane, or polytetrafluoroethylene (PTFE), or a metal rich in superelastic characteristics such as nickel alloy.

In addition, a filter to be used as the filter 31 may have any pore size in a range making it possible to capture plaques and the like with a bloodstream secured. In a sheet having pores formed therein, the pore diameter is preferably 30 to 500 μm, and in a mesh, it is preferably formed such that one side of the mesh opening is 30 to 500 μm. In addition, the surface of the filter may undergo antithrombotic treatment.

The filter 31 of the filter device 1 is not only freely rotatable relative to the core member 21 and but also movable along the core member 21. Because of this, the filter is allowed to be stably indwelled without following any predetermined range of movement during an atherectomy surgery when the filter device is used together with an atherectomy device.

The material of the ring 32 may be any one as long as the opening diameter of the ring can be expanded or reduced in the direction perpendicular to the longitudinal direction and as long as the material is a bendable and flexible wire material having elasticity or shape-memory ability. The filter opening is itself extended outwardly in the direction perpendicular to the longitudinal direction, and thus enhances the contact to the inner wall of a blood vessel, making it possible to reliably capture emboli such as thrombi and foams generated in an endovascular treatment and the like.

Among others, a suitable material to be used for the ring 32 is one which is rich in superelastic characteristics and thus can change variously in shape and also be restored to the original ring shape. Because of this, the material is preferably formed of a shape-memory polymer or shape-memory alloy, more preferably nickel alloy.

In addition, it is desirable that the ring 32 has an X-ray contrast property so that the indwelling in a blood vessel can be recognized. A method of imparting an X-ray contrast property may be one in which part or the whole of the ring 32 contains an X-ray contrast material. Examples of X-ray contrast materials that can be used include gold, platinum, tungsten, palladium alloy and the like.

The ring 32 fixed to the opening is preferably constituted by a wire extendable in the direction perpendicular to the longitudinal direction and having elasticity or shape-memory ability. The opening of the filter section 3 is itself extended outwardly in the direction perpendicular to the longitudinal direction, and thus enhances the contact to the inner wall of a blood vessel, making it possible to reliably capture emboli such as thrombi and foams generated in an endovascular treatment and the like.

The opening of the filter section 3 preferably has an opening diameter of approximately 40 to 80 mm, for example, when the filter device is indwelled in the lower-extremity peripheral artery. The filter section 3 preferably has a filter length of approximately 10 to 50 mm.

It is preferable that the first wires 41 include a plurality of wires, and also that the wires are disposed opposite to each other or substantially equiangularly in relation to the central axis of the core member 21. It is preferable that the second wires 42 also include a plurality of wires, and also that the wires are disposed opposite to each other or substantially equiangularly in relation to the central axis of the core member 21.

Furthermore, it is preferable that the first wires 41 and the second wires 42 are disposed alternately and equiangularly in relation to the central axis. This constitution allows the opening diameter of the opening of the filter section 3 to be reduced in a favorable manner. Specifically, the first wires 41 and the second wires 42 of the filter device 1 according to the first example are provided, two wires each, as depicted in FIG. 1, and the one ends of the first wires 41 and the second wires 42 are alternately fixed to the ring 32 at intervals such that the central angle in relation to the central axis is 90 degrees. The other ends of the first wires 41 may be fixed to the third tube 25, and the other ends of the second wires 42 may be fixed to the second tube 24.

The positions at which the first wires 41 are fixed to the ring 32 and the positions at which the second wires 42 are fixed to the ring 32 are preferably alternately disposed in relation to the central axis of the core member 21, as above-mentioned, because the opening of the filter 3 is thereby deformed in a favorable manner.

In addition, in a filter device 12 according to an example different from the first example, a first wire group 411 or a second wire group 421, which is composed of a plurality of wires, may be formed as the first wires 41 or the second wires 42. In this example, the wire groups are constituted by a plurality of wires disposed at intervals such that the central angle in relation to the central axis of a reference wire is 0 degrees to 45 degrees.

Figure 5:
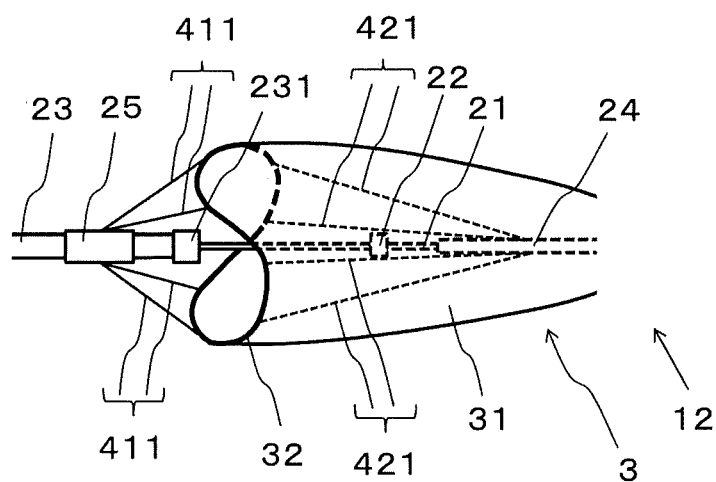
FIG. 5 is an explanatory view depicting a fourth example of a filter device.

Regarding how the wires are combined, either combination is possible: a combination of wires and a wire group such as between the first wires 41 and the second wire group 421 or a combination of wire groups such as between the first wire group 411 and the second wire group 421. It is preferable that the first wires 41 or the first wire group 411 and the second wires 42 or the second wire group 421 are disposed alternately and equiangularly in relation to the central axis. This constitution allows the opening diameter of the opening of the filter section 3 to be reduced in a favorable manner. Specifically, as described in FIG. 5 depicting a filter device according to a fourth example, the first wire group 411 composed of two wires and the second wire group 421 composed of two wires in the same manner are provided, two sets each. The two wires constituting the first wire group 411 and the two wires constituting the second wire group 422 are spaced such that the central angle in relation to the central axis is 45 degrees each between two wires, and in addition, one end of the first wire group 411 and one end of the second wire group 421 are fixed to the ring 32 alternately at intervals such that the central angle in relation to the central axis is 90 degrees. In this example, the other ends of the first wire groups 411 are fixed to the third tube 25, and the other ends of the second wires 42 are fixed to the second tube 24.

The material to be used for the first wires 41 and the second wires 42 may be a polymer such as polyester, polyacrylate, polyurethane, or polytetrafluoroethylene (PTFE), or a metal rich in superelastic characteristics such as nickel alloy. When the above-mentioned polymers are used, it is possible that the polymers are coated with a rigid material such as polyimide to enhance the pushing force of the wire.

Figure 6:
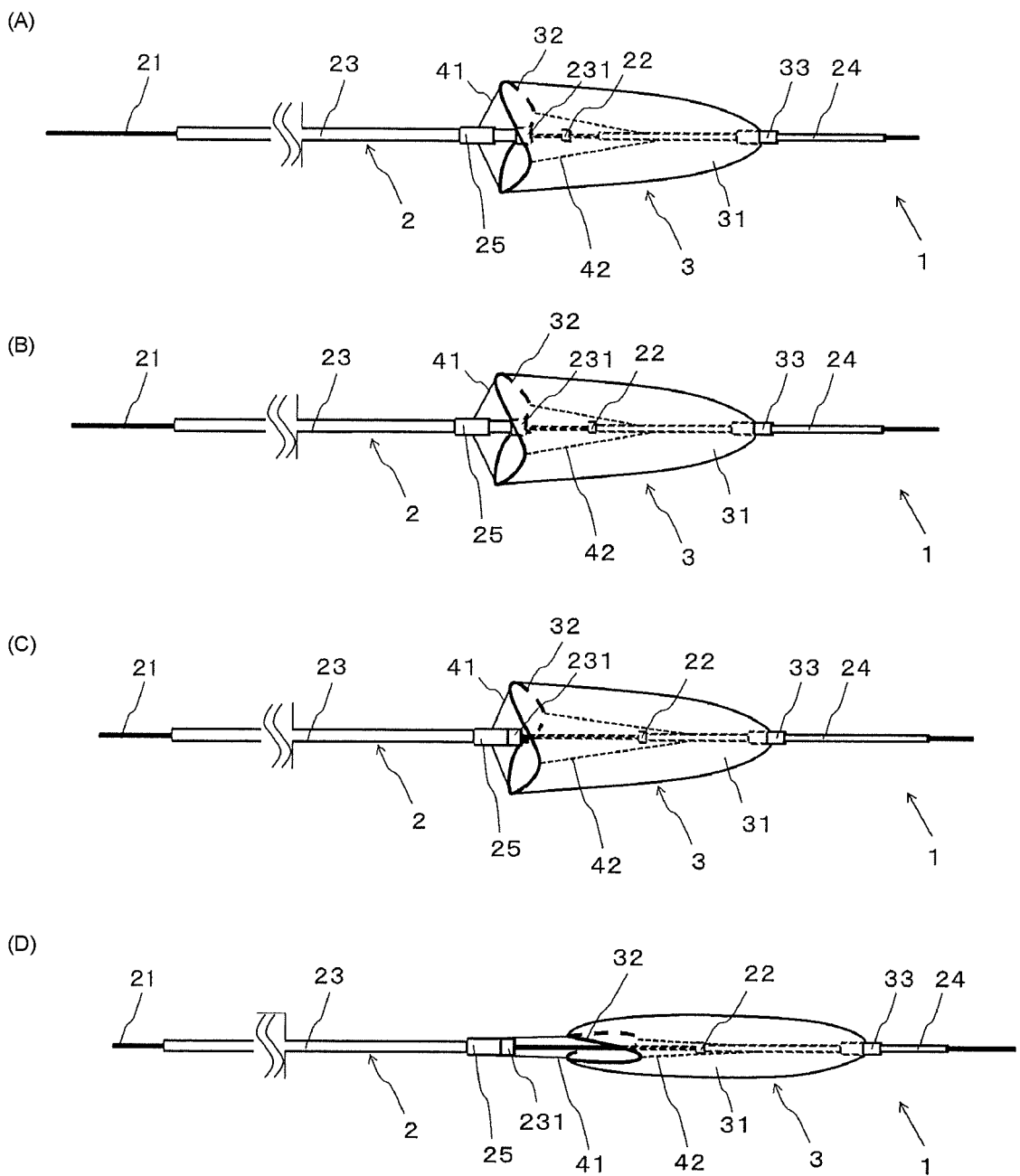
FIGS. 6(A)-(D) are explanatory views depicting a process in which the diameter of the opening of a filter device according to the first example is reduced.

With the filter device 1 according to the first example, the core member 21 is pushed relative to the first tube 23, whereby the opening diameter of the opening of the filter section 3 can be reduced, as described in FIG. 6 depicting the process of reducing the opening diameter of the opening. Specifically, the core member is pushed, causing the push member 22 to move and come in contact with the proximal side of the second tube 24 in the longitudinal direction. Further application of a push causes the push member 22 to push the second tube 24 outward and, thus, the second tube 24 is moved to a distal portion of the core member 21 in the longitudinal direction. In this example, the movement of the second tube 24 in the distal direction causes force to be transmitted to the ring 32 via the second wires 42 fixed to the second tube 24 and causes force to be transmitted to the third tube 25 via the first wires 41 fixed to the ring 32. This causes the filter section 3 and the third tube 25 to move in the longitudinally distal direction. In this example, the third tube 25 finally comes in contact with the first restriction member 231. Further application of a push to the core member 21 causes the second tube 24 to move continuously in the distal direction although the first restriction member 231 stops the third tube 25 from moving in the distal direction. Thus, the distance between the second tube 24 and the third tube 25 is extended. As the distance between the second tube 24 and the third tube 25 is extended, the second wires 42 are pulled without moving the position of the first wires 41, and thus, the ring 32 is deformed to reduce the opening diameter of the opening of the filter section 3.

In this manner, the above-mentioned filter device 1 makes it possible that the push member 22 fixed to the core member 21 is pushed with the push member 22 in contact with the second tube 24, causing the first wires 41 and the second wires 42 to deform the shape of the ring 32 and thus reduce the diameter of the opening of the filter 31. Contrarily, releasing the push member 22 fixed to the core member 21 from the second tube 24 causes the shape of the ring 32 to be restored and thus expands the diameter of the opening of the filter 31.

Figure 7:
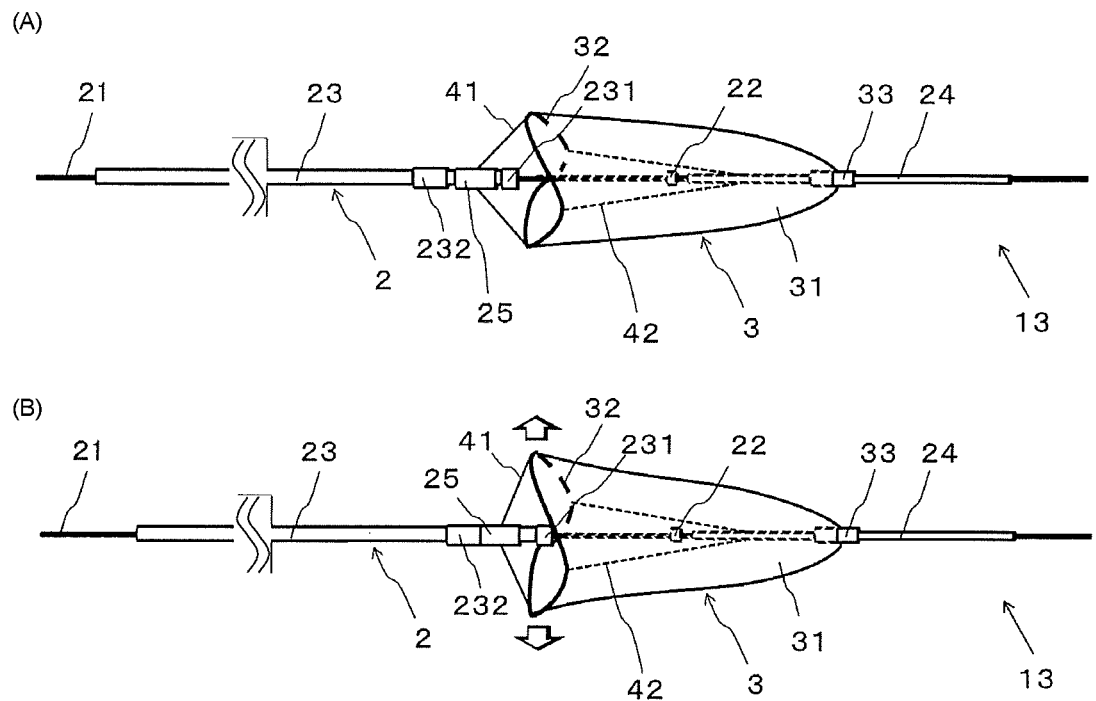
FIGS. 7(A)-(B) are explanatory views depicting a fifth example of a filter device.

As described in FIG. 7, a filter device 13 according to a fifth example different from the first example may include a second restriction member 232 that is fixed proximally of the third tube 25 along the first tube 23 and restricts the movement of the third tube 25 in the longitudinally proximal direction. This constitution makes it possible that the ring 32 is adhered to the blood vessel wall in a good manner. Specifically, the filter section 3 is deployed in a blood vessel, the first tube 23 is then pushed in the distal direction relative to the core member 21, whereby the second restriction member 232 is moved to a distal portion of the core member 21 in the longitudinal direction, and comes in contact with the proximal side of the third tube 25 in the longitudinal direction. A further push of the first tube 23 causes outward force acting on the blood vessel wall to be transmitted to the ring 32 via the first wires 41 fixed to the second tube 24, thus enhancing the contact of the ring 32 to the blood vessel wall.

Figure 8:
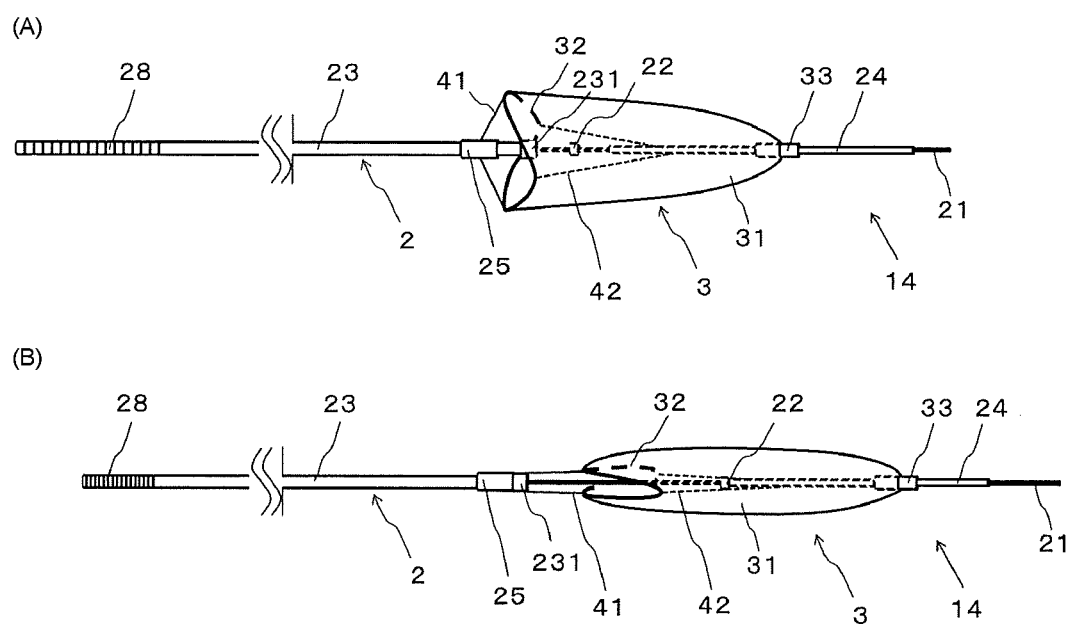
FIGS. 8(A)-(B) are explanatory views depicting a sixth example of a filter device.

A spring-like member 28 may be fixed to a proximal portion of the core member 21 in the longitudinal direction as depicted in FIG. 8, in a filter device 14 according to a sixth example different from the first example. With this constitution, a push of the core member 21 in the direction of the filter causes the first tube 23 to come in contact with the spring-like member 28, causing the filter to be compressed and deformed into a form shorter than the natural length. A push of the core member 21 reduces the opening diameter of the opening of the filter section 3, and then, stopping a load on the core member 21 causes the spring-like member 28 to be restored to the natural state and causes the opening diameter of the opening of the filter section 3 to be naturally expanded.

The material that can be used for the spring-like member 28 is stainless steel, superelastic alloy, cobalt alloy, nickel alloy, palladium alloy, tungsten or the like.

Figure 9:
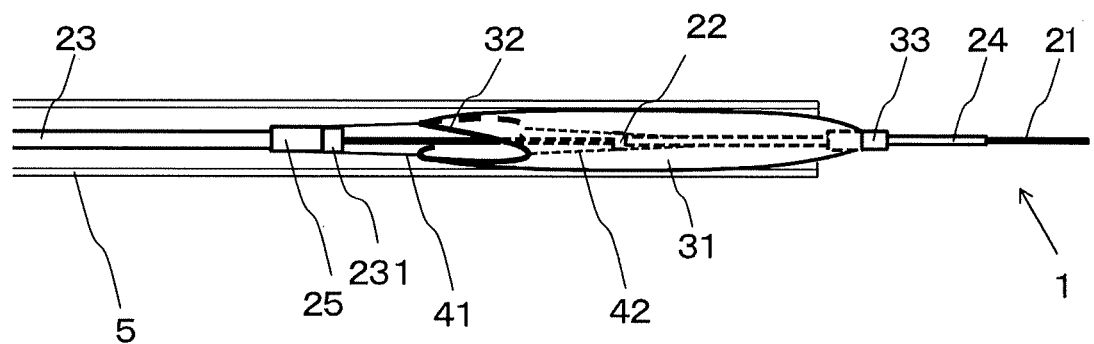
FIG. 9 is an explanatory view depicting the state where a filter device is delivered.

With the filter device 1 according to this first example, the body section 2 and the filter section 3 may be inserted into a tubular member 5, as described in FIG. 9 depicting the state of the filter device being delivered. This constitution enables the filter device to pass through a narrowed area with the opening diameter of the filter section 3 reduced, and thus allowing easy delivery to a target affected site.

EXAMPLES

Below, specific Examples of a filter device 1 will be described with reference to the drawings.

Example 1

A filter device 1 described in FIG. 1 was produced. In Example 1, a stainless steel wire having a diameter of 0.21 mm and a length of 1200 mm was used as a core member 21.

As a push member 22, a polyimide tube having an inside diameter of 0.24 mm, a thickness of 0.06 mm, and a length of 20 mm was used. The core member 21 was inserted into the tube, which was then fixed to the core member using an adhesive.

A first tube 23 had a three-layered structure: an inner layer of polytetrafluoroethylene, an interlayer of stainless steel braids, and an outer layer of polyimide, and the tube used had the following approximate dimensions: 0.37 mm in outside diameter, 0.24 mm in inside diameter, and 1000 mm in length. The core member 21 was inserted into the tube. In this example, the first tube 23 was disposed proximally of the push member 22.

As a second tube 24, a polyimide tube having an inside diameter of 0.18 mm, a thickness of 0.02 mm, and a length of 20 mm was used, and the core member 21 was inserted into the tube. In this example, the second tube 24 was disposed distally of the push member 22.

As a third tube 25, a polyimide tube having an inside diameter of 0.45 mm, a thickness of 0.08 mm, and a length of 3 mm was used, and the first tube 22 was inserted into the third tube.

As a first restriction member 231, a polyimide tube having an inside diameter of 0.45 mm, a thickness of 0.03 mm, and a length of 3 mm was used, and the first tube 23 inserted into the first restriction member, which was then fixed to a distal portion of the first tube 23 in the longitudinal direction using an adhesive.

A filter 31 was formed in bag shape using a mesh that was made of polyester fiber monofilaments having a line diameter of 28 μm and that had a mesh opening having a 100 μm side. The opening, when opened, alternately had a plurality of mountains protruding in the longitudinally distal direction and a plurality of valleys sinking in the longitudinally proximal direction.

A ring 32 was formed by quintuplicately winding a nickel-titanium alloy wire having a line diameter of 48 μm, and processing the wire so that the resulting ring could have a diameter of 6 mm and a longitudinal length of 3 mm and have mountains and valleys, two each, spaced alternately and equally and having a wavelike shape as a whole. In addition, the ring 32 was fixed to the filter 31 using polyurethane, and the filter section 3 was produced to have a full length of approximately 33 mm (including the ring 32).

As the first wires 41 and the second wires 42, polyacrylate fibers coated with polyimide and having a line diameter of 60 μm were used, two each. The first wires 41 had their proximal ends fixed to the third tube 25 and their distal ends fixed to the bottoms of the valleys of the ring 32. The second wires 42 had their proximal ends fixed to the tops of the mountains of the ring and their distal ends fixed to the second tube 24.

Comparative Example 1

Figure 10:
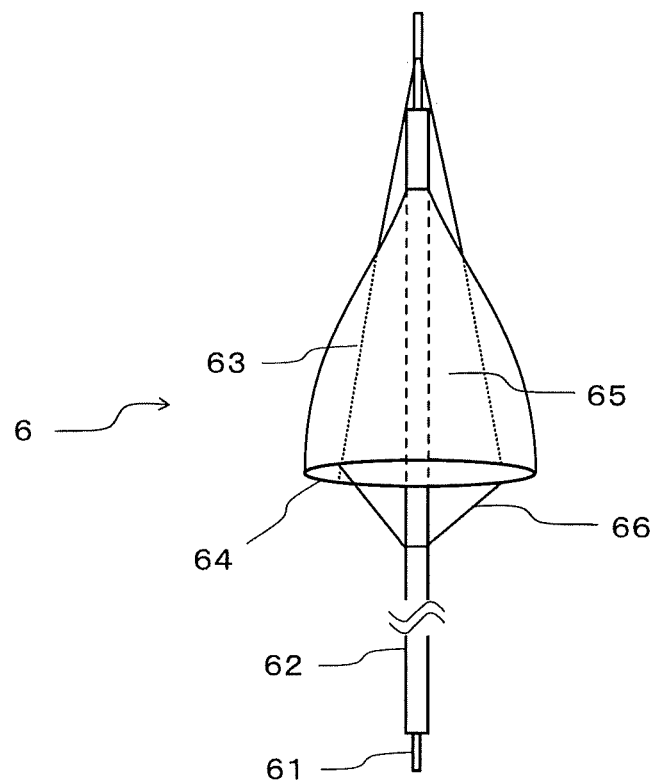
FIG. 10 is an explanatory view depicting the intravascular blood filter in Comparative Example 1.

In Comparative Example 1, an intravascular blood filter 6 described in JP '353 was produced. Specifically, as described in FIG. 10, the filter included: a core member 61; a catheter member 62 slidable along the core member 61; a filter 63 having its distal end opened and its proximal end fixed to the distal portion of the catheter member 62; a filter ring 64 provided on the opening of the filter member 63 and configured to help fold and extend the filter member 63; two forward traction wires 65 connecting the filter ring 64 and a distal portion of the core member 61; and two backward traction wires 66 connecting the filter opening/closing member 63 and the catheter member 62 in the filter member 63. The intravascular blood filter 6 enables its opening to be closed by moving the core member 61 relative to the catheter member 62 to deform the filter.

As the core member 61, a stainless steel wire having an outside diameter of 0.21 mm and a length of 1200 mm was used.

The catheter member 62 had a three-layered structure: an inner layer of polytetrafluoroethylene, an interlayer of stainless steel braids, and an outer layer of polyimide, and a tube used as the catheter member had the following approximate dimensions: 0.37 mm in outside diameter, 0.24 mm in inside diameter, and 1000 mm in length. The core member 61 was inserted into the lumen.

The filter member 63 was formed using a mesh that was made of polyester fiber monofilaments having a line diameter of 28 μm and that had a mesh opening having a 100 μm side. In addition, the filter member 63 had its distal end fixed to a distal portion of the catheter member 62 so that the proximal end of the filter member could be the opening.

A filter ring 64 was formed by quintuplicately winding a nickel-titanium alloy wire having a line diameter of 48 μm, and processing the wire so that the ring could be a loop having an opening diameter of 6 mm. In addition, the filter ring 54 was fixed to the filter 53 using polyurethane, and the filter section 53 was produced to have a full length of approximately 30 mm.

As the forward traction wires 65, polyester fibers having a line diameter of 60 μm, two each, were used, one end of each wire was fixed to the filter ring 64, and the other end was fixed to a distal portion of the core member 61.

As the backward traction wires 66, polyester fibers having a line diameter of 60 μm, two each, were used, one end of each wire was fixed to the filter ring 54, and the other end was fixed to a distal portion of the catheter member 52.

In this regard, the forward traction wires 65 and the backward traction wires 66 were fixed to the filter ring 54 to be spaced alternately such that the central angle in relation to the central axis of the catheter member 52 is 90 degrees.

Comparative Example 2

In Comparative Example 2, a peripheral protection device 9 (Spider FX (registered trademark); manufactured by Covidien Ltd.) was used, wherein the opening diameter of the opening of the filter was 6 mm when expanded. The peripheral protection device 9 was in the shape of a structure in which a distal portion of a shaft had, attached thereto, a filter for capturing and retrieving embolic matter and in which a core shaft was disposed on the periphery of the opening of the filter.

Experiment in Torsion Caused by Rotation

The intravascular blood filter 6 described in Comparative Example 1 was deployed in a mimic blood vessel tube 7 having a diameter of 5 mm, and along the intravascular blood filter 6, an atherectomy device 8 was inserted. Then, one rotation was applied to the atherectomy device 8 and, as a result, the forward traction wires 65 were entwined with the core member 61, the catheter member 62, and the filter member 63, and the backward traction wires 66 were entwined with the catheter member 62, causing torsion to the filter member 63. Application of one more rotation caused the filter member 63 to result in opening insufficiently.

When the intravascular blood filter 6 in Comparative Example 1 was used together with an atherectomy device, the filter was found to follow a predetermined range of movement during an atherectomy surgery, causing the traction wires to be entwined with the core member, the catheter member, or the filter member 63. In this example, the filter section was twisted, thus causing the filter section to have a smaller volume capable of capturing emboli such as resected pieces. Furthermore, it is possible that the opening of the filter section results in being insufficiently controlled, letting emboli generated in a surgery pass downstream.

Figure 11:
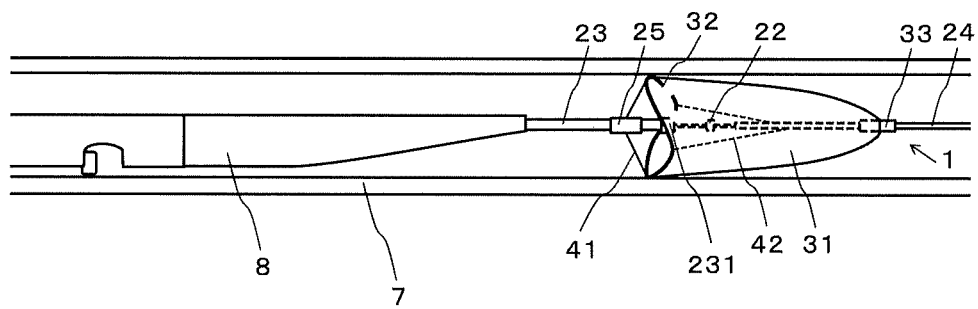
FIG. 11 is an explanatory view depicting an experiment system for experimenting in torsion caused by application of rotation.

On the other hand, as described in FIG. 11 depicting an experiment system for experimenting in torsion caused by rotation, the filter device 1 described in Example 1 was deployed in a mimic blood vessel tube 7, and an atherectomy device 8 was inserted along the filter device 1, followed by application of rotation to the atherectomy device 8, with the result that the filter section 3 caused no torsion and had no insufficient opening. As above-mentioned, the filter device 1 described in Example 1 can be indwelled without following any predetermined range of movement during an atherectomy surgery when the filter device is used together with an atherectomy device.

Experiment in Capture at Curved Portion with Mimic Emboli Particles

Figure 12:
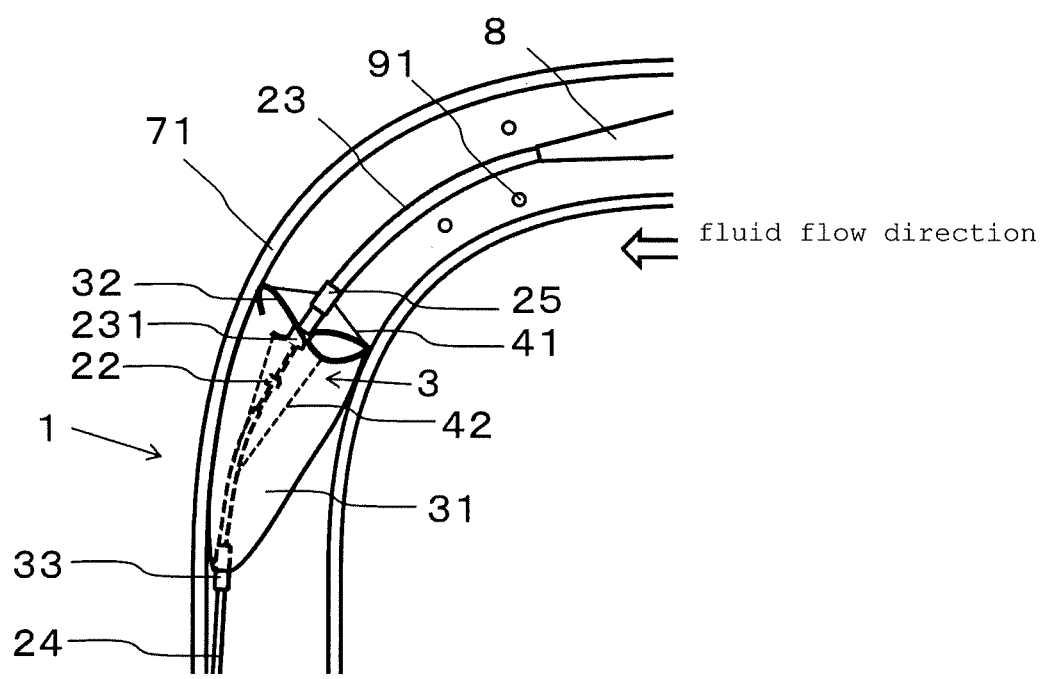
FIG. 12 is an explanatory view depicting an experimental system for a capture rate experiment carried out using mimic emboli particles.

A mimic blood vessel tube 71 that had a curved portion having a radius of curvature of 40 mm and had an inside diameter of 5 mm was provided. The mimic blood vessel tube 71 was filled with an aqueous solution of 44 wt % glycerin. As described in FIG. 12, the filter device 1 described in Example 1 was indwelled at the top of the curved portion, followed by inserting an atherectomy device 8 along the filter device 1. In this example, the filter section 3 of the filter device 1 was disposed approximately 20 mm away from the distal end of the atherectomy device 8. Then, mimic embolic particles 91 in spherical shape and having a diameter of 300 μm were fed into the mimic blood vessel tube 71 through a position upstream of the position where the filter device 1 described in Example 1 was indwelled. After the mimic embolic particles 91 were fed, the atherectomy device 8 was pulled out, and subsequently, the core member 21 was pushed relative to the first tube 23, whereby the opening diameter of the opening of the filter section 3 was reduced, and then the filter device 1 was retrieved. The retrieval was followed by measurement of the number of the mimic embolic particles 91 captured and retrieved in the filter section 3 of the filter device 1 and measurement of the number of the mimic embolic particles 91 that had passed downstream through the filter section 3 of the filter device 1. The ratio of the number of the mimic embolic particles 91 captured and retrieved by the filter device 1 described in Example 1 was expressed as a percentage to the number of the mimic embolic particles 91 fed into the mimic blood vessel tube 71, and the percentage was regarded as a capture rate. The capture rate exhibited by the filter device 1 in Example 1 was found to be 99% or more. In this regard, the number of the mimic embolic particles 91 fed into the mimic blood vessel tube 71 was calculated by adding the number of the mimic embolic particles captured and retrieved in the filter section 3 to the number of the mimic embolic particles that had passed downstream through the filter section 3.

Comparative Example 2 was used to carry out an experiment in capture at the curved portion using the mimic embolic particles 91 in the same manner, and the capture rate was found to be 87%.

We found the following: the peripheral protection device 9 in Comparative Example 2 had a core shaft disposed on the periphery of the opening of the filter; the peripheral protection device 9 was indwelled at the curved portion, followed by inserting the atherectomy device 8; the core shaft of the peripheral protection device 9 was pulled in the direction of the central axis of the mimic blood vessel tube by the atherectomy device 8, causing voids to be generated in the space on the wall of the mimic blood vessel; and the mimic emboli particles passed downstream through the voids, resulting in lowering the capture rate. In contrast, the filter device 1 described in Example 1 did not have the body section 2 mounted on the circumference of the ring 32, and thus, did not cause such a phenomenon as caused in Comparative Example 2.

INDUSTRIAL APPLICABILITY

Our filter device is indwelled downstream of a treated site, for example, when an atherectomy surgery is performed to treat lower-extremity arteriosclerosis obliterans. The filter device thus makes it possible to protect peripheral vessels by preventing emboli such as resected pieces from being carried away into peripheral vessels and from causing infarction, in which the resected pieces are generated in performing an atherectomy surgery.

The invention claimed is:

1. A filter device comprising:
   a core member;
   a push member fixed to said core member;
   a first tube disposed proximally of said push member in a longitudinal direction and movable along said core member;
   a second tube disposed distally of said push member in the longitudinal direction and movable along said core member;
   a third tube movable along said first tube;
   a first restriction member disposed on said first tube and configured to restrict a pushing movement of said third tube to the distal direction of said first restriction member;
   a filter having a closed end distally of said push member in the longitudinal direction and disposed to have an opening at a proximal end of said filter;
   a ring fixed to said opening and having elasticity or shape-memory ability;
   two first wires, one end of each first wire fixed to said third tube, and the other end fixed to part of said ring; and
   two second wires, one end of each second wire fixed to part of said ring, and the other end fixed to said second tube,
   wherein said filter is configured such that a diameter of said opening is reduced by deformation of the shape of said ring, the deformation caused by said first wires and said second wires when said push member fixed to said core member is pushed with said push member in contact with said second tube, and such that the diameter of said opening is expanded by restoration of said ring to an original shape, the restoration caused by separating said push member fixed to said core member from said second tube.

2. The filter device according to claim 1, wherein positions at which said first wires are fixed to the said ring and positions at which said second wires are fixed to said ring are arranged alternately in relation to the central axis of said core member.

3. The filter device according to claim 1, wherein a second restriction member is fixed to said first tube and configured to restrict the movement of said third tube to a proximal portion of said first tube in the longitudinal direction.

4. The filter device according to claim 1, wherein a spring-like member is fixed to a proximal portion of said core member in the longitudinal direction.

5. The filter device according to claim 1, wherein a flexible member is fixed to a distal portion of said core member in the longitudinal direction.

6. The filter device according to claim 1, comprising:
a double lumen tube having a first lumen into which a guidewire can be inserted and a second lumen into which said core member can be inserted,
wherein said double lumen tube is fixed to a distal portion of said second tube in the longitudinal direction.

* * * * *